(12) United States Patent
Ortmaier et al.

(10) Patent No.: US 8,740,881 B2
(45) Date of Patent: Jun. 3, 2014

(54) STERILE BARRIER FOR A SURGICAL ROBOT WITH TORQUE SENSORS

(75) Inventors: Tobias Ortmaier, Hemmingen (DE); Dirk Jacob, Augsburg (DE); Thomas Neff, Munich (DE); Achim Heinze, Augsburg (DE)

(73) Assignee: KUKA Laboratories GmbH, Augsburg (DE)

( * ) Notice: Subject to any disclaimer, the term of this patent is extended or adjusted under 35 U.S.C. 154(b) by 828 days.

(21) Appl. No.: 12/810,430

(22) PCT Filed: Jan. 20, 2009

(86) PCT No.: PCT/EP2009/050577
§ 371 (c)(1),
(2), (4) Date: Jun. 24, 2010

(87) PCT Pub. No.: WO2009/092701
PCT Pub. Date: Jul. 30, 2009

(65) Prior Publication Data
US 2010/0292707 A1 Nov. 18, 2010

(30) Foreign Application Priority Data
Jan. 24, 2008 (DE) .................. 10 2008 005 901

(51) Int. Cl.
*A61B 17/00* (2006.01)
(52) U.S. Cl.
USPC ....... 606/1; 606/14; 606/19; 606/32; 606/253
(58) Field of Classification Search
None
See application file for complete search history.

(56) References Cited

U.S. PATENT DOCUMENTS

| 2002/0111713 A1 | 8/2002 | Wang et al. |
| 2006/0161138 A1 | 7/2006 | Orban, III et al. |
| 2006/0235436 A1 | 10/2006 | Anderson et al. |

FOREIGN PATENT DOCUMENTS

| DE | 20 2007 006 121 U1 | 9/2007 | |
| EP | 1 754 448 A1 | 2/2007 | |
| FR | 2 683 479 A1 | 5/1993 | |
| FR | WO 99/08841 | * 2/1999 | ............... B25J 19/00 |
| WO | 99/08841 A1 | 2/1999 | |
| WO | 03/037755 A2 | 5/2003 | |
| WO | 2007/122717 A1 | 11/2007 | |

OTHER PUBLICATIONS

Machine Translation of FR2683479.
European Patent Office; Search Report in International Patent Application No. PCT/EP2009/050577 dated Apr. 16, 2009; 6 pages.

* cited by examiner

*Primary Examiner* — Gary Jackson
*Assistant Examiner* — Scott T. Luan
(74) *Attorney, Agent, or Firm* — Wood, Herron & Evans, LLP

(57) ABSTRACT

The invention relates to a sterile barrier (S) for a surgical robot (1) comprising at least one joint (12 ... 15) with two opposing joint members (40, 42) that rotate relative to one another about a common joint axis (16 ... 19) and a torque sensor (29) comprising: at least two sterile barrier sections (24 ... 28) each with an end section (38, 39) for sealed attachment to a respective joint end section (41, 43) of the joint member (40, 42); and a sealing arrangement (30) for producing a sterile and sealed rotating connection of the end sections (38, 39) of the at least two sterile barrier sections (24 ... 28); and a surgical robot (1).

14 Claims, 3 Drawing Sheets

STERILE BARRIER FOR A SURGICAL ROBOT WITH TORQUE SENSORS

Figure 1:
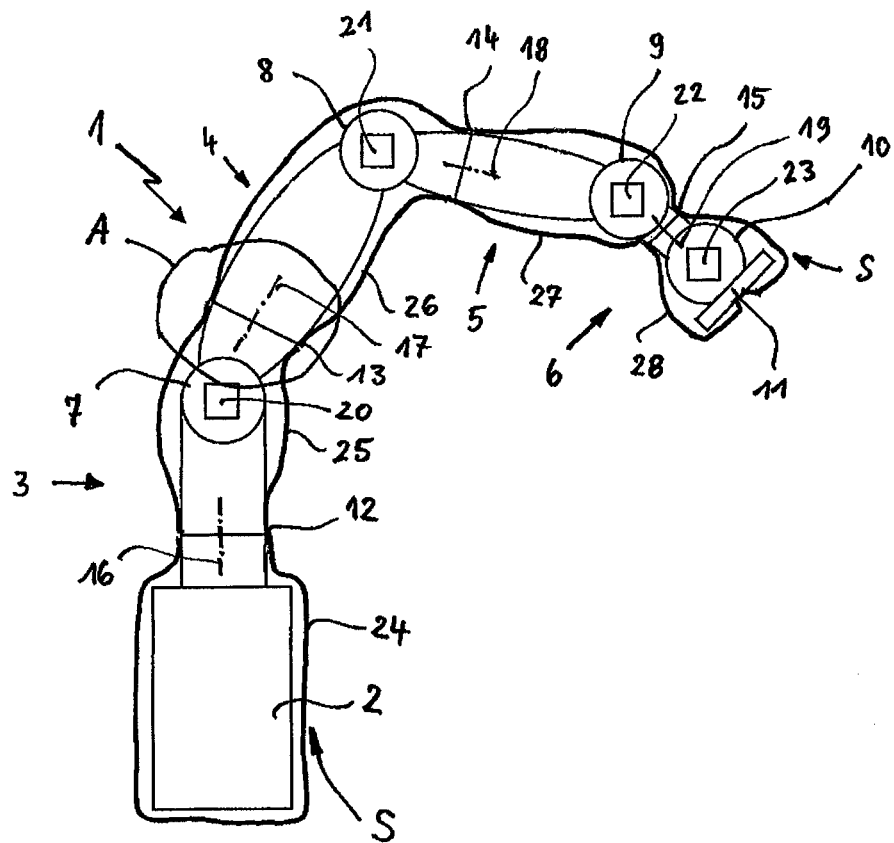

The invention relates to a sterile barrier for a surgical robot having at least one joint with two opposing joint members that are rotatable relative to one another about a common joint axis and a torque sensor.

Surgical robots are manipulating machines which are equipped with relevant tools, for example on a so-called flange, for automatic and/or guided performance of surgical working procedures on patients in human and/or veterinary medicine, and are programmable or controllable in a plurality of axes of motion, in particular with regard to orientation, position and process sequence.

In addition to normal operating instruments, technical equipment such as the endoscope, surgical microscope and drill are being used more and more frequently in surgical operations. The utilization is subject to strict hygiene requirements. As soon as such a device is put to use in an operation and contact is made with the patient—even if only indirectly—, the sterility of the contact surface must be assured. The contact surface is normally the entire outer surface of the device. Current sterilization techniques (such as steam sterilizing) are not suitable or only conditionally suitable for electrical and electronic equipment. In order to achieve sterility nevertheless, sterile plastic or rubber covers, so-called sterile barriers, are generally pulled over the (inherently non-sterile) device, or are used to give the device a sterile covering.

In the case of surgical robots, the problem arises in this connection that the freedom of movement of the robot must not be restricted by the sterile cover. To prevent the risk of the cover tearing, the cover may for example be designed very loosely. As a result, the cover may be able to get into the working area of the surgeon. For that reason it is often fixed as close as possible to the robot with adhesive tape.

When a surgical robot is equipped with torque sensors in the joints, covers that are too tight or that are modified with adhesive tape may cause additional a priori unknown moments to act on the torque sensor; this is especially true when the robot is moving. The result is that a function such as gravitation compensation, for example, which uses the readings of both the joint angle sensors and the torque sensors, may deliver erroneous results. Regulating procedures such as impedance, force or admittance regulation may also no longer be able to function, or only to a very limited extent, due to faulty torque sensor values. For that reason, in all of the possible relevant positions and configurations of the robot, no additional moments, in particular no unpredictable or estimable moments, or only very slight ones, may act on the torque sensors in the course of an operation due to a sterile barrier for such a robot.

Examples of sterile barriers on surgical robots are described for example in U.S. 20060161138 A1 and U.S. 020060235436 A1. Those publications do not address the problems of the torque sensors.

The object of the invention is therefore to specify a sterile barrier for surgical robots with torque sensors, which eliminates or significantly reduces the above disadvantages in comparison to the existing art.

Another object of the invention is to specify a corresponding surgical robot.

The problem of the invention is solved by a sterile barrier for a surgical robot having at least one joint with two opposing joint members that are rotatable relative to one another about a common joint axis and a torque sensor, having at least two sterile barrier sections, each having an end section for sealed attachment to a respective joint end section of the joint members, and a sealing arrangement for producing a continuous sterile and sealed rotating connection of the end sections of the at least two sterile barrier sections.

This ensures the unrestricted mobility of the surgical robot, while at the same time eliminating or nearly eliminating any retroactive effect on the torque sensors in every relevant robot position and configuration. At the same time, optimized, i.e., time-saving, placement and removal of the sterile barrier is achieved.

Through the use of a sterile barrier of plastic or rubber in at least two parts (so-called drapes), whose individual sections begin in each case before and after the positions of the torque sensors on the surface of the housing, influence of the cover on these sensors can be prevented or reduced. To enable the entire surface of the robot to be covered with the sterile barrier, the gaps in the area of the joints with the torque sensors between the individual sections of the sterile barrier named above must be bridged over.

To that end, the sealing arrangement has the following: an inner ring, to be attached tightly to the joint end section of the first joint member of the joint, an outer ring having an attaching section for attaching to the joint end section of the second joint member of the joint and provided with a sealing section for overlapping the inner ring, and a sealing element provided to be positioned between the inner ring and the sealing section of the outer ring, to seal the inner ring relative to the outer ring.

The outer ring reaches over the joint gap and over the inner ring, and has a section with a larger diameter than the inner ring. That produces an overlap between inner and outer ring, which is closed by a sealing element, for example a sterile sealing ring of rubber. That makes the sterile barrier of the robot continuous.

For rapid assembly and disassembly, the inner ring and the outer ring each have a locking device for securing and releasing.

The two rings are rotatable relative to each other when the robot is in use, so that the readings of the torque sensors are not falsified by the friction of the sealing element. To that end, for example to reduce the friction and at the same time to increase the tightness of the seal, the inside of the sealing section of the outer ring and the outside of the inner ring may be provided with an appropriate coating and/or surface treatment in the area of the bearing surface for the sealing element. Through the use of appropriate disturbance observers in the automatic control system, it is possible to identify the additional friction which arises when the rings and the sealing element move relative to each other, and to compensate or allow for it in the control system.

In order to obtain the necessary flexibility of the sterile barrier sections, they can be kept looser in the area of joints or moving parts. That prevents stretching or tearing at the maximum articulation angle. In the area of connecting elements, in which a user grasps the robot to guide or control it manually, for example to change the configuration, the sterile barriers can be made tighter.

The starting and end positions of the sterile barrier sections must be defined exactly, in order to ensure a continuous sterile covering. To that end, the end sections of the sterile barrier sections may be designed with at least one flexible clamping element each to fix them and interact with a corresponding recess on the respective joint end section. These recesses are for example circumferential channels or grooves, in which the end sections, equipped for example with elastic, are received.

The same problem arises in the exact positioning of the sealing arrangement. Here it is preferred that the inner ring and the outer ring each have a continuous nose to interact with a respective groove on the corresponding joint end section. The nose may be formed for example with a trapeze-shaped cross section. That results in fast, exact positioning of the sealing arrangement by the rings retracting unassisted into the grooves, as well as increasing the seal.

The end sections of the sterile barrier sections can also be provided for interacting with corresponding mounting sections of the inner and outer rings for sealing and attaching to the latter and the respective joint end sections, by placing the end sections together with the noses in the trapezoidal grooves and having them pressed into the grooves by the noses, achieving a seal.

The inner ring and outer ring are preferably made of a sterilizable material and/or a combination of sterilizable materials, for example, a suitable metal such as stainless steel. They may also be provided with spring elements or elastic sections, in order to increase a clamping force to seal and fix the sterile barrier end sections. In another preferred embodiment, these elements are produced as one-time-use or consumable articles.

Alternatively, the sealing element may be firmly connected to the inner ring or to the outer ring. A sterile fitted cut or a sterilizable fitted cut of a continuous product is also possible.

A surgical robot according to the invention having at least one joint with a torque sensor has at least one sterile barrier described above.

Figure 2:
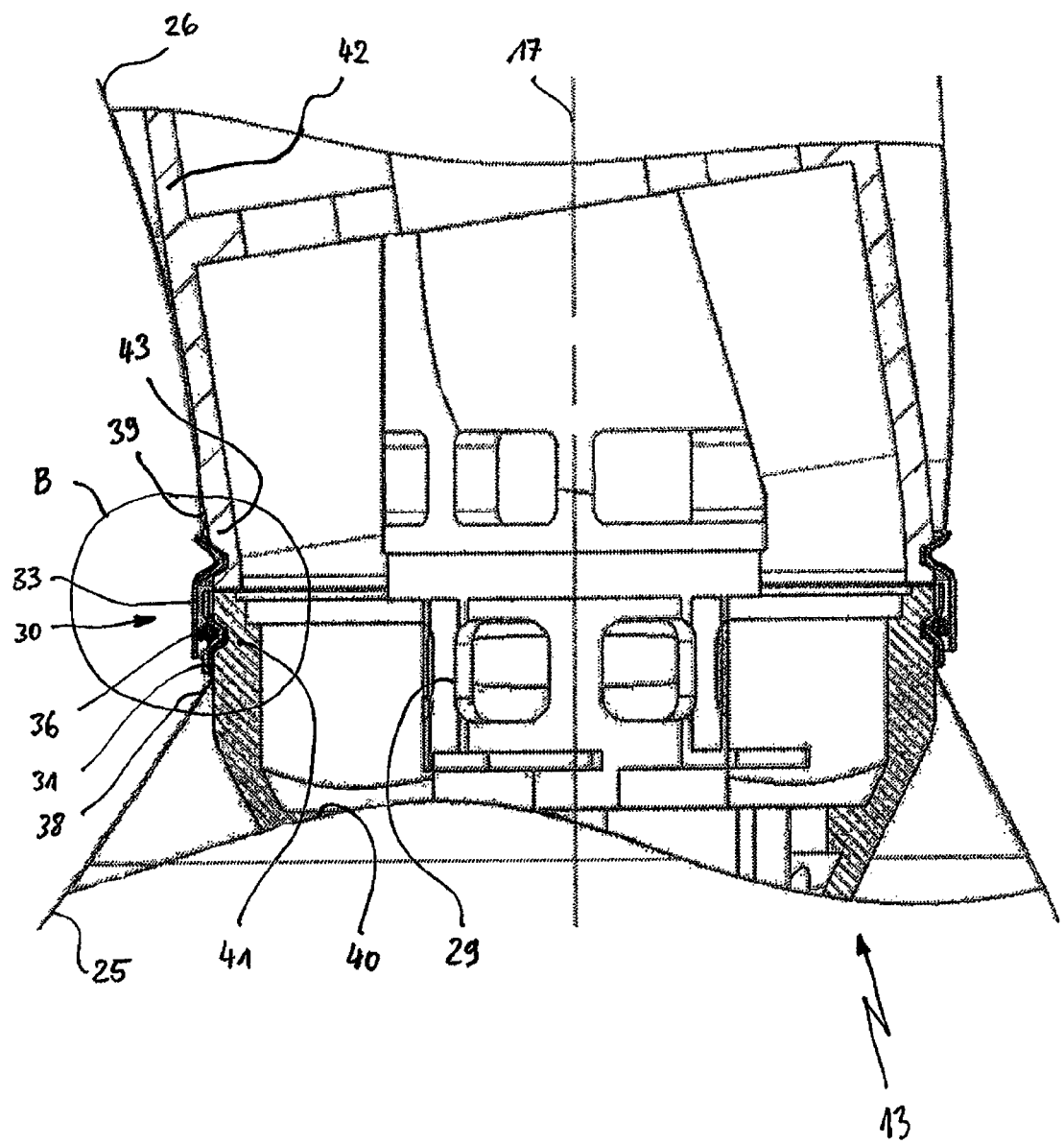
Figure 3:
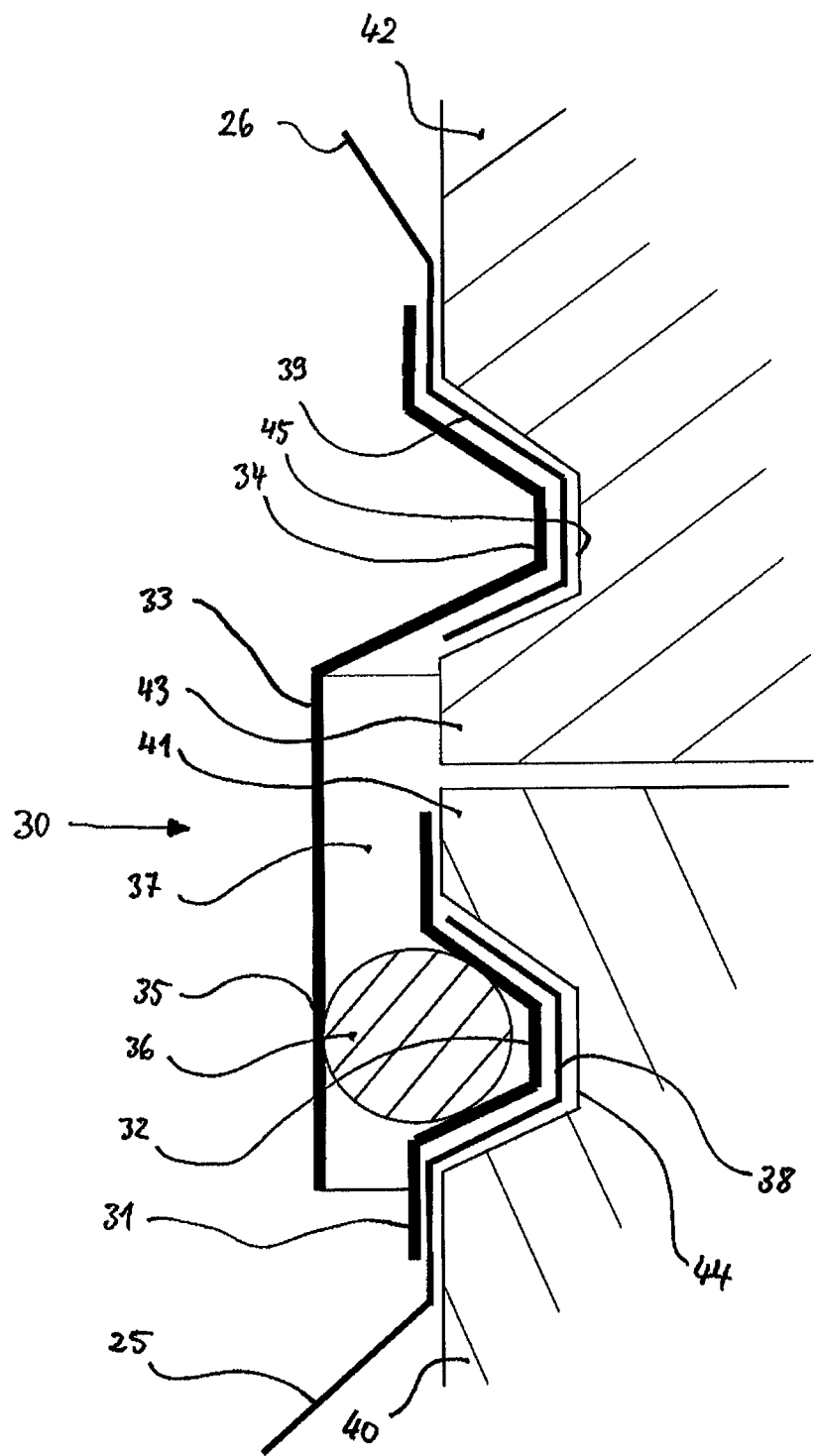

Examples of exemplary embodiments of the invention are depicted in the accompanying schematic drawing. The figures show the following:

FIG. 1 an exemplary schematic depiction of a surgical robot with a sterile barrier according to the invention, FIG. 2 an enlarged partial sectional view of area A of a joint of the surgical robot according to FIG. 1, and FIG. 3 an enlarged schematic partial sectional view of area B of the joint according to FIG. 2.

Like components or components with the same function are designated in the figures with the same reference labels.

FIG. 1 depicts an exemplary embodiment of a surgical robot 1 with a sterile barrier S according to the invention.

Robot 1 has 8 axes in this case: four joint axes 16 through 19 and four articulated joint axes 20 through 23.

Axis 16 is a vertical rotational axis of a pedestal 2 relative to a base 3 of robot 1. Articulated joint axis 20 connects base 3 with a first arm 4 in a first articulated joint 7 transverse to axis 16. Arm 4 is subdivided into two parts, which are rotatable around axis 17 in their longitudinal axis. The other end of the first arm 4 is swivel-connected with a second articulated joint 8 around the second articulated joint axis 21 to a second arm 5, which like the first arm 4 is made up of two parts, which are rotatable around axis 18 in their longitudinal axis. Attached at the other end of the second arm 5 in a like manner is a third articulated joint 9 with an articulated joint axis 22, which is connected to articulated joint axis 23 via a two-part hand piece 6 with a hand joint 10. Hand piece 6 also has two parts here, which are rotatably connected in their longitudinal axis around the fourth axis 19, i.e., a hand joint axis. A flange 11 for a tool (not shown) is situated on the hand joint 10.

For use in an operating room, robot 1 is completely covered with a sterile cover, a sterile barrier S according to the invention. Sterile barrier S does not exert any unwanted retroactive effects on torque sensors 29, which are situated in joint axes 16 through 19, as may be seen in FIG. 2. To this end, sterile barrier S is executed in multiple pieces, in this example five, sterile barrier sections 24 through 28, each of which encloses a robot section and which are attached in the joints 12, 13, 14, 15, in each case at the ends of joints 12 through 15. A first sterile barrier section 24 encloses pedestal 2 and the lower part of base 3, a second sterile barrier section 25 encloses the upper part of base 3, first articulated joint 7 and the lower part of first arm 4, a third sterile barrier section 26 encloses the upper part of first arm 4 and the lower part of second arm 5 with second articulated joint 8, a fourth sterile barrier section 27 encloses the upper part of second arm 5 with third articulated joint 9 and the lower part of hand piece 10, and finally, a fifth sterile barrier section 28 encloses the upper part of hand piece 10 and hand joint 19 with flange 11. Thus the individual robot sections, for example the upper part of arm 4 with second articulated joint 8 and the additional sections attached to it, can turn relative to the lower part of arm 4, without the sterile barrier sections, in this case 25 and 26, becoming twisted and influencing the torque sensors 29. This will now be described in greater detail in connection with FIG. 2.

FIG. 2 shows an enlarged partial sectional view of area A as an exemplary depiction of joint 13 of surgical robot 1 according to FIG. 1.

In joint 13, the lower part of first arm 4 (see FIG. 1) as a first joint member 40 with a joint end section 41, and the upper part of first arm 4 as a second joint member 42 with a joint end section 43, are connected rotatably around joint axis 17. Situated on joint axis 17 between the two joint end sections 41 and 43, which are opposite each other, is torque sensor 29, not described in further detail.

Tightly fastened to joint end sections 41 and 43 are end sections 38 and 39 of second and third sterile barrier sections 25 and 26, in the area of a sealing arrangement 30. Sealing arrangement 30 has an inner ring 31, which is applied here to joint end section 41 in a groove. On the opposite joint end section 43, an outer ring 33 of sealing arrangement 30 is fixed in another groove in a similar way. Outer right 33 overlaps inner ring 31 in the direction of joint axis 17 by a certain length, and has a diameter in this area that is larger than the outside diameter of inner ring 31. A sealing element 36 is situated in this area.

End sections 38 and 39 of sterile barrier sections 25 and 26 are attached to joint end sections 41 and 43 respectively under inner ring 31 and outer ring 33 of sealing arrangement 30, so that a tight and sterile bridging over of joint 13 is formed. Joint members 40 and 42 are turnable relative to each other, with sterile barriers 25 and 26 and rings of sealing arrangement 30 situated on them turning together with them. Between the rings and sealing element 36 a calculable or identifiable friction value prevails, which can be included with the speed of rotation in a regulating procedure, whereby the disturbances in the readings of torque sensor 29 caused by the frictional forces can be substantially compensated for.

The sealing arrangement 30 in area B is shown in an enlarged view in FIG. 3.

FIG. 3 depicts an exemplary embodiment in which it can be seen clearly that end sections 38 and 39 of sterile barrier sections 25 and 26 are tightly attached respectively in trapezoidal grooves 44, 45 under trapezoidal noses of rings 31 and 33. In a mounting section 32 of the nose of inner ring 31, sealing element 36 is kept with a circular cross section, for example a round core sealing ring of rubber. The other side of sealing element 36 rests tightly against the inner surface of sealing section 35 of outer ring 33. Thus an intermediate space 37 formed between rings 31 and 33 is likewise tight against the outside of sealing arrangement 30. Outer ring 33 has a mounting section 34 for mounting it on joint end section 43 and sealing section 35. Other forms are of course conceivable. It is important that the surfaces of sterile barrier sections 25 and 26 be connected tightly and sterilely through sealing arrangement 30.

Sterile barrier S can be assembled especially simply and quickly. To that end, the individual sterile barrier sections 24 through 28 are pulled over the corresponding robot sections. Then the inner rings 31 are attached with quick release fasteners, which are not shown here. Next the sealing elements 36 and the outer rings 33, which also have quick release fasteners, are put on. This begins with inner ring 31 on joint 12 (see FIG. 1).

The sterile barrier S according to the invention is not limited to the versions described and depicted in the figures. Modifications and changes in conjunction with the accompanying claims are possible.

In a particular design, articulated joints can also be equipped with the sterile barrier S according to the invention and the sealing arrangement 30. To that end, the articulated joints must at least have joint end sections for mounting the respective end sections of the sterile barrier sections and sealing arrangements.

The invention claimed is:

1. A sterile barrier for use with a surgical robot, the surgical robot having a torque sensor and at least one joint defined by first and second opposing joint members rotatable relative to one another about a common joint axis, the sterile barrier comprising:
   a first sterile barrier section having a proximal end and a distal end, the distal end of the first sterile barrier section configured to be sealingly coupled to the second joint member, and
   a second sterile barrier section having a proximal end and a distal end, the distal end of the second sterile barrier section configured to be sealingly coupled to the second joint member; and
   a sealing assembly sealingly coupled to the first and second sterile barrier sections and permitting rotation of the first and second sterile barrier sections relative to one another, the sealing assembly including:
   an inner ring configured for coupling to the first joint member,
   an outer ring configured for coupling to the second joint member, at least a portion of the outer ring being disposed about at least a portion of the inner ring so as to define an overlapping section of the inner and outer rings with one another, and
   a sealing element disposed between and sealing against the inner and outer rings in the overlapping section.

2. The sterile barrier of claim 1, wherein the inner ring includes an inner ring locking device and the outer ring includes an outer ring locking device to selectively secure the inner and outer rings in place relative to the first and second joint members, respectively.

3. The sterile barrier of claim 1, wherein:
   the first joint member includes a first groove,
   the second joint member includes a second groove,
   the inner ring has an inner ring nose section configured to be received within the first groove, and
   the outer ring has an outer ring nose section configured to be received within the second groove.

4. The sterile barrier of claim 1, wherein at least a portion of the inner ring and at least a portion of the outer ring comprise a sterilizable material.

5. The sterile barrier of claim 4, wherein the sterilizable material is stainless steel.

6. The sterile barrier of claim 1, wherein the first joint member includes a groove, the inner ring includes a nose section configured to be received within the groove, and the sealing element is positioned and sized so as to be supported within the groove.

7. The sterile barrier of claim 1, wherein the first joint member includes a first recess and the second joint member includes a second recess, the sterile barrier further comprising:
   a first flexible clamping element cooperating with the first recess to secure the first sterile barrier section in place relative to the first joint member, and
   a second flexible clamping element cooperating with the second recess to secure the second sterile barrier section in place relative to the second joint member.

8. The sterile barrier of claim 1, wherein:
   the inner ring is configured to secure the first sterile barrier section in place relative to the first joint member, and
   the outer ring is configured to secure the second sterile barrier section in place relative to the second joint member.

9. The sterile barrier of claim 8, wherein:
   the first joint member includes a first groove,
   the second joint member includes a second groove,
   the inner ring has an inner ring nose section configured to engage a portion of the first sterile barrier section in the first groove to thereby secure the first sterile barrier section relative to the first joint member, and
   the outer ring has an outer ring nose section configured to engage a portion of the second sterile barrier section in the second groove to thereby secure the second sterile barrier section relative to the second joint member.

10. A sterile barrier for use with a surgical robot, the surgical robot having a torque sensor and at least one joint defined by first and second opposing joint members rotatable relative to one another about a common joint axis, the sterile barrier comprising:
   a first sterile barrier section having a proximal end and a distal end, the distal end of the first sterile barrier section configured to be sealingly coupled to the first joint member;
   a second sterile barrier section having a proximal end and a distal end, the distal end of the second sterile barrier section configured to be sealingly coupled to the second joint member; and
   a sealing assembly sealingly coupled to the first and second sterile barrier sections and permitting rotation of the first and second sterile barrier sections relative to one another, the sealing assembly including:
   an inner ring configured for coupling to the first joint member,
   an outer ring configured for coupling to the second joint member, at least a portion of the outer ring being disposed about at least a portion of the inner ring so as to define an overlapping section of the inner and outer rings with one another, and
   a sealing element disposed between the inner and outer rings in the overlapping section;
   wherein the sealing element is firmly connected to the inner ring or to the outer ring.

11. A sterile barrier for use with a surgical robot, the surgical robot having a torque sensor and at least one joint defined by first and second opposing joint members rotatable relative to one another about a common joint axis, the sterile barrier comprising:

a first sterile barrier section having a proximal end and a distal end, the distal end of the first sterile barrier section configured to be sealingly coupled to the first joint member;

a second sterile barrier section having a proximal end and a distal end, the distal end of the second sterile barrier section configured to be sealingly coupled to the second joint member; and a sealing assembly sealingly coupled to the first and second sterile barrier sections and permitting rotation of the first and second sterile barrier sections relative to one another, the sealing assembly including:

an inner ring configured for coupling to the first joint member, an outer ring configured for coupling to the second joint member, at least a portion of the outer ring being disposed about at least a portion of the inner ring so as to define an overlapping section of the inner and outer rings with one another, and a sealing element disposed between the inner and outer rings in the overlapping section;

wherein the sealing element is a sterile fitted element or a sterilizable fitted element.

12. A sterile barrier for use with a surgical robot, the surgical robot having a torque sensor and at least one joint defined by first and second opposing joint members rotatable relative to one another about a common joint axis, the first joint member having a first groove and the second joint member having a second groove, the sterile barrier comprising:

a first sterile barrier section having a proximate end and a distal end, the distal end of the first sterile barrier section configured to be sealingly coupled to the first joint member;

a second sterile barrier section having a proximate end and a distal end, the distal end of the second sterile barrier section configured to be sealingly coupled to the second joint member; and a sealing assembly sealingly coupled to the first and second sterile barrier sections and permitting rotation of the first and second sterile barrier sections relative to one another, the sealing assembly including:

an inner ring including a first nose section configured to be received within the first groove, an outer ring having a second nose section configured to be received within the second groove, at least a portion of the outer ring being disposed about at least a portion of the inner ring so as to define an overlapping section of the inner and outer rings with one another, and a sealing element disposed between the inner and outer rings in the overlapping section and positioned and sized so as to be supported within the first groove.

13. A surgical robot, comprising:

at least one joint defined by first and second opposing joint members rotatable relative to one another about a common joint axis;

a torque sensor positioned so as to sense a torque associated with rotational movement of the first and second joint members relative to one another; and a sterile barrier positioned so as to block access to the torque sensor, the sterile barrier having:

a first sterile barrier section having a proximal end and a distal end, the distal end of the first sterile barrier section being sealingly coupled to the first joint member, a second sterile barrier section having a proximal end and a distal end, the distal end of the second sterile barrier section being sealingly coupled to the second joint member, and a sealing assembly sealingly coupled to the first and second sterile barrier sections and permitting rotation of the first and second sterile barrier sections relative to one another, the sealing assembly including:

an inner ring coupled to the first joint member, an outer ring coupled to the second joint member, at least a portion of the outer ring being disposed about at least a portion of the inner ring so as to define an overlapping section of the inner and outer rings with one another, and a sealing element disposed between and sealing against the inner and outer rings in the overlapping section.

14. The surgical robot of claim 13, further comprising:

a controller operatively coupled to the first and second joint members and to the torque sensor; and a detector operatively coupled to the controller and configured to detect the friction associated with rotation of the first and second sterile barrier sections relative to one another and to generate a signal to the controller associated with the detected friction, wherein, in response to the generated signal, the controller is configured to compensate the torque value received from the torque sensor.

* * * * *

UNITED STATES PATENT AND TRADEMARK OFFICE
CERTIFICATE OF CORRECTION

| | | |
|---|---|---|
| PATENT NO. | : 8,740,881 B2 | Page 1 of 1 |
| APPLICATION NO. | : 12/810430 | |
| DATED | : June 3, 2014 | |
| INVENTOR(S) | : Tobias Ortmaier et al. | |

It is certified that error appears in the above-identified patent and that said Letters Patent is hereby corrected as shown below:

In the Specification:

Column 2,
Lines 11-12 read "placement and removal of the sterile barrier is achieved." and should read
-- placement and removal of the sterile barrier are achieved. --.

Column 3,
Line 34 reads "depicted in the accompanying schematic drawing." and should read -- depicted in the accompanying schematic drawings. --.

In the Claims:

Claim 1, Column 5,
Line 33 reads "configured to be sealingly coupled to the second joint" and should read -- configured to be sealingly coupled to the first joint --.

Signed and Sealed this
Ninth Day of December, 2014

Michelle K. Lee
*Deputy Director of the United States Patent and Trademark Office*